(12) United States Patent
Yamazaki et al.

(10) Patent No.: US 7,390,644 B2
(45) Date of Patent: *Jun. 24, 2008

(54) PRODUCTION OF EXOPOLYSACCHARIDES UNATTACHED TO THE SURFACE OF BACTERIAL CELLS

(75) Inventors: Motohide Yamazaki, San Diego, CA (US); Marcia Mikolajczak, Encinatas, CA (US); Thomas J. Pollock, San Diego, CA (US); Richard W. Armentrout, La Jolla, CA (US)

(73) Assignees: Shin-Etsu Bio., Inc., San Diego, CA (US); Shin-Etsu Chemical Company, Ltd., Tokyo (JP)

( * ) Notice: Subject to any disclaimer, the term of this patent is extended or adjusted under 35 U.S.C. 154(b) by 298 days.

This patent is subject to a terminal disclaimer.

(21) Appl. No.: 10/617,371

(22) Filed: Jul. 10, 2003

(65) Prior Publication Data

US 2004/0077056 A1 Apr. 22, 2004

Related U.S. Application Data

(62) Division of application No. 09/905,829, filed on Jul. 13, 2001, now Pat. No. 6,605,461.

(60) Provisional application No. 60/220,145, filed on Jul. 24, 2000.

(51) Int. Cl.
- C08B 37/00 (2006.01)
- C12N 1/20 (2006.01)
- C12N 1/12 (2006.01)
- C12P 17/02 (2006.01)
- C12P 19/04 (2006.01)
- C12P 1/04 (2006.01)

(52) U.S. Cl. ............... 435/252.1; 435/170; 435/72; 435/41; 435/252.3; 435/101; 536/123; 536/123.1

(58) Field of Classification Search ............... 536/123, 536/123.1; 435/101, 72, 41, 170
See application file for complete search history.

(56) References Cited

U.S. PATENT DOCUMENTS

| | | | |
|---|---|---|---|
| 3,915,800 A | 10/1975 | Kang et al. | 195/31 P |
| 3,960,832 A | 6/1976 | Kang et al. | 536/123 |
| 4,326,052 A | 4/1982 | Kang et al. | |
| 4,326,053 A | 4/1982 | Kang et al. | 536/123 |
| 4,342,866 A | 8/1982 | Kang et al. | 536/119 |
| 4,401,760 A | 8/1983 | Peik et al. | 435/101 |
| 4,963,668 A | 10/1990 | Allen et al. | 536/114 |
| 5,300,429 A | 4/1994 | Baird et al. | 435/101 |
| 5,338,681 A | 8/1994 | Deckwer et al. | 435/252.1 |
| 5,602,241 A | 2/1997 | Maruyama et al. | 536/127 |
| 5,854,034 A | 12/1998 | Pollock et al. | 435/101 |
| 5,985,623 A | 11/1999 | Pollock et al. | 435/101 |
| 6,027,925 A | 2/2000 | Pollock et al. | 435/104 |
| 6,030,817 A | 2/2000 | Pollock et al. | 435/104 |
| 6,066,479 A | 5/2000 | Wright et al. | 435/101 |

FOREIGN PATENT DOCUMENTS

EP 266163 A2 5/1988

OTHER PUBLICATIONS

ATCC Catalogue of Bacteria and Bacteriophages, 19th edition, 1996, pp. 26, 68 and 295.

Lobas et al., "Structure and Physical Properties of the Extracellular Polysaccharide PS-P4 Produced by *Sphingomonas paucimobilis* P4 (DSM 6418)," *Carbohydrate Research*, 251 (1994) 303-313.

Banik R. M. et al: "Exopolysaccharide of Gellan Family: Prospects and Potential." *World Journal of Microbiology & Biotechnology*, vol. 16, No. 5, Jul. 2000, pp. 407-414, ISSN: 0959-3993.

Jay A. J. et al: "Analysis of Structure and Function of Gallans with Different Substitution Patterns." Carbohydrate Polymers, vol. 35, No. 3-4. Mar. 4, 1998, pp. 179-188, ISSN: 0144-8617.

Pollock T. J. et al: "Planktonic/Sessile Dimorphism of Polysaccharide-Encapsulated Sphingomonads." *Journal Of Industrial Microbiology And Biotechnology*, vol. 23, No. 4/5. 1999, pp. 436-441, XP0010303946, ISSN: 1367-5435.

Manna B. Et al, "Production and Rheological Characteristics of the Microbial Polysaccharide Gellan." *Letters In Applied Microbiology*, vol. 23, No. 3, 1996, pp. 141-145, XP001031116, ISSN: 0266-8254.

Baird et al., "Industrial Applications of Some New Microbial Polysaccharides," *Biotechnology*, Nov. 1983, pp. 778-783.

Fialho et al., "Structures and Properties of Gellan Polymers Produced by *Sphingomonas paucimobilis* AATCC 31461 form Lactose Compared with Those Produced from Gluscose and from Cheese Whey", *AEM*, vol. 65, No. 6, Jun. 1999, pp. 2485-2491.

(Continued)

*Primary Examiner*—Ruth A Davis
*Assistant Examiner*—Sheridan R MacAuley
(74) *Attorney, Agent, or Firm*—Seed IP Law Group PLLC

(57) ABSTRACT

The present invention is directed to a *Sphingomonas* bacteria and a method of producing exopolysaccharides by culturing a *Shpingomonas* bacteria in a fermentation broth for a time and temperature effective for providing a sphingan exopolysaccharide in a slime form.

10 Claims, No Drawings

OTHER PUBLICATIONS

Harding et al., "Isolation of Genes Essential for the Biosynthesis of Gellan Gum," *The FASEB Journal*, vol. 7, No. 7, May 1993, p. A1259.

Jansson et al., "Structural Studies of Gellan Gum, an Extracellular Polysaccharide Elaborated by *Pseudomonas elodea*," *Carboydrate Research*, 124, 1983, pp. 135-139.

Kang et al., "A New Bacterial Heteropolysaccharide," Extracellular Microbial Polysaccharides, 1977, pp. 220-230.

Kang et al., "Agar-Like Polysaccharide Produced by a *Pseudomonas* Species: Production and Basic Properties," *AEM*, vol. 43, No. 3, 1982, pp. 1086-1091.

Kang et al., "Some Novel Bacterial Polysaccharides of Recent Development," *Progress in Industrial Microbiology*, vol. 18, 1983, pp. 231-253.

Kelco Biopolymer Product Information, "Products Gellan Gum", Feb. 2000.

Kuo et al., "Isolation and Location of L-Glycerate, an Unusual Acyl Substituent in Gellan Gum," *Carbohydrate Research*, 156, 1986, pp. 173-187.

Moorhouse et al., "PS-60: A New Gel-Forming Polysaccharide," Solution Properties of Polysaccharides, 1981, pp. 111-124.

Moorhouse, "Structure/Property Relationships of a Family of Microbial Polysaccharides," Industrial Polysaccharides: Genetic Engineering, Structure/Property Relations and Applications, 1987, pp. 187-206.

Nussinovitch, "Gellan Gum," Hydrocolloid Applications, 1997, pp. 63-82. Pollock, "Gellan-related Polysaccharides and the genus *Sphingomonas*," *J. of Gen Microbiol.*, vol. 139, 1993, pp. 1939-1945.

Pollock et al., "Planktonic/sessile Dimorphism of Polysaccharide-Encapsulated Sphingomonads," *JIMB*, vol. 23, 1999, pp. 436-441.

Pollock et al., "Production of Xanthan Gum by *Sphingomonas* bacteria Carrying Genes from *Xanthomonas campestris*," *JIMB*, vol. 19, 1997, pp. 92-97.

Pollock et al., "Mechanism of Bacitracin Resistance in Gram-Negative Bacteria That Synthesize Exopolysaccharides," *J. of Bacteriol.*, vol. 176, No. 20, 1994, pp. 6229-6237.

Pollock et al., "Assignment of Biochemical Functions to Glycosyl Transferase Genes Which are Essential for Biosyntheis of Exopolysaccharides in *Sphingomonas* Strain S88 and *Rhizobium leguminosarum*," *J. of Bacteriol.*, vol. 180, No. 3, 1998, pp. 586-593.

Thorne et al., "Increasing the Yield and Viscosity of Exopolysaccharides Secreted by *Sphingomonas* by Augmentation of Chromosomal Genes with Multiple Copies of Cloned Biosynthetic Genes," *JIMB*, vol. 25, 2000, pp. 49-57.

Vartak et al., "Glucose Metabolism in '*Sphingomonas elodea*': pathway engineering via construction of a glucose-6-phosphate dehydrogenase insertion mutant," *Microbiology*, vol. 141, 1995, pp. 2339-2350.

Videira et al., "Identification of the pgmG Gene, Encoding a Bifunctional Protein with Phosphoglucomutase and Phosphomannomutase Activities, in the Gellan Gum-Producing Strain *Sphingomonas paucimobilis* ATCC 31461," *Appl. Environ Microbiol.*, vol. 66, No. 5, 2000, pp. 2252-2258.

Yamazaki et al., "Linkage of Genes Essential for Synthesis of a Polysaccharide Capsule in *Sphingomonas* Strain S88," *J. Bacteriol.*, vol. 178, No. 9, 1996, pp. 2676-2687.

PRODUCTION OF EXOPOLYSACCHARIDES UNATTACHED TO THE SURFACE OF BACTERIAL CELLS

CROSS-REFERENCE TO RELATED APPLICATIONS

This application is a divisional of U.S. patent application Ser. No. 09/905,829, filed Jul. 13, 2001 now U.S. Pat. No. 6,605,461, now allowed, which application claims the benefit of U.S. Provisional Patent Application No. 60/220,145, filed Jul. 24, 2000, wherein these applications are incorporated herein by reference in their entireties.

The present invention relates to the production of exopolysaccharides and bacteria for the production of exopolysaccharides. More particularly, the bacteria of the present invention produce exopolysaccharides in a slime form that is unattached to the surface of the bacterial cell.

BACKGROUND

There is an ever increasing demand for inexpensive and environmentally acceptable viscosifiers, bioemulsifiers and biodegradable polymers. Exopolysaccharides are an example of compounds that are useful for these purposes because of their distinctive rheological properties. Exopolysaccharides, such as for example gellan, welan and rhamsan, are produced commercially for applications in foods, cosmetics, and in oil-field production, and for other applications. Each exopolysaccharide displays a different characteristic set of aqueous rheological properties including resistance to shear, compatibility with various ionic compounds, and stability to extreme temperatures, pH and salt concentrations.

Exopolysaccharides can be produced through bacterial fermentations. Different strains of the genus Sphingomonas produce exopolysaccharides including gellan, welan, rhamsan, S-88, S-7, S-198, NW11, and S-657, to name some examples (Pollock 1993, J. Gen. Microbiol. 139:1939-1945). There are many other exopolysaccharides made by other strains of *Sphingomonas* bacteria. The exopolysaccharides produced by *Shpingomonas* bacteria are referred to as "sphingans" with reference to the common genus as a source. At least three sphingans (gellan, welan, and rhamsan) are produced commercially by large scale submerged fermentation.

The biotechnology industry has responded to the demand for exopolysaccharide compounds by increasing the availability of a variety of bacterial exopolysaccharide products that are acceptable for commercial use. Although many of the bacterial exopolysaccharide products offer a wide range of attractive improvements over synthetically produced materials, they remain relatively expensive to produce. The expense is generally associated with costs of recovery and purification of the desired product.

Higher fermentation yields of exopolysaccharides have occurred as a result of improvements and alterations of bacterial strains, and better understanding of bacterial biosynthesis and optimization of fermentation conditions. This satisfies one of the important steps in recovering adequate amounts of the polymer for potential industrial applications. However, increased exopolysaccharide concentration in the fermentation process results in increased viscosities which require higher inputs of energy to effectively disperse oxygen and nutrients in the fermentation broth. Hence, fermentations that provide higher exopolysaccharide yields have resulted in correspondingly higher production costs.

Recovery of exopolysaccharides remains a difficult and costly step. Bacterial strains from the genus *Shpingomonas* produce exopolysaccharides which remain attached to the cell surface (Pollock et al. 1999, J. Indust. Microciol. Biotechnol. 23: 436-441). The attached polymers form a capsule around the bacteria. The capsule of polysaccharide is not readily separated from the bacteria. Even after diluting a fermentation broth with sufficient water to reduce the viscosity, the capsule remains attached to the bacterial cells and the cells cannot be separated from the capsule by centrifugal sedimentation. Other physical or chemical methods are required to separate the cells from the capsule. For example, partial hydrolysis of the polysaccharides with acid can be used to release most of the polysaccharide from the cells by randomly breaking the polymer chains near to the point of attachment to the cell.

Recovery of exopolysaccharide, regardless of the conditions used to produce it, typically involves a precipitation step. The precipitated exopolysaccharide is then recovered by centrifugation. A typical method for recovering gellan and welan gums is a follows. Immediately after fermentation the culture broths are heated to at least 90° C. to kill the living bacteria. Both gums are then separated from the culture broth by precipitation with approximately 2 volumes of isopropylalcohol, and the precipitated polysaccharide fibers are collected, pressed, dried and milled. The alcohol is recovered by distillation. In this most simple process the polysaccharide remains attached to the cells, such that when the dried and milled polysaccharides is resuspended in water the solution is not transparent. In the case of gellan gum additional steps can be introduced to purify the polysaccharide away from the bacterial cells so that the resuspended product is more transparent. Before the alcohol precipitation, the culture broth is centrifuged or filtered or both while the temperature is maintained above the critical transition temperature between a highly viscous state and a liquefied state which is amenable to centrifugation or filtration. These processes are disclosed in U.S. Pat. No. 4,326,052 (gellan); U.S. Pat. No. 4,326,053 (gellan); U.S. Pat. No. 4,342,866 (welan); U.S. Pat. No. 3,960,832 (S-7); and U.S. Pat. No. 4,535,153 (S-88), which are hereby incorporated by reference.

A major inefficiency associated with a typical product recovery protocol is incomplete recovery of the exopolysaccharide. Bacterial exopolysaccharides are attached to the producing cells with varying degrees of tenacity. Those bacteria that have relatively securely attached exopolysaccharides are less likely to shed them into the medium, thus reducing the amount of exopolysaccharide available for recovery in the precipitation step and increasing the process steps needed to separate the exopolysaccharides from the producing cells.

Advantages, features and characteristics of the present invention will become more apparent upon consideration of the following description and the appended claims.

SUMMARY

The present invention is directed to a method of producing sphingan exopolysaccharides and *Shpingomonas* bacteria that produce the sphingan exopolysaccharides. The present invention provides a method where the sphingan exopolysaccharides are produced in a slime form such that the sphingan exopolysaccharide is unattached to the surface of the *Shpingomonas* bacteria. Production of the sphingan exopolysaccharide in a slime form requires less energy as compared to fermentations where the exopolysaccharide remains attached to the bacterial cell in a capsule form. Further, separation and recovery of sphingan exopolysaccharide produced in a slime form is more efficient as compared to recovery of sphingan exopolysaccharide produced in a capsule form.

In one aspect, the present invention provides a method for producing sphingan exopolysaccharides that includes culturing *Shpingomonas* bacteria in a fermentation broth for a time and temperature effective for providing a sphingan exopolysaccharide in a slime form. In an important aspect of the invention, *Shpingomonas* bacteria that have been genetically mutated to produce a slime form of sphingan exopolysaccharide, are utilized in a submerged fermentation. Examples of genetically mutated *Shpingomonas* bacteria include ATCC PTA-3487 (strain X287), ATCC PTA-3486 (strain X530), ATCC PTA-3485 (strain Z473), ATCC PTA-3488(strain X031), and mixtures thereof.

Fermentation of the genetically mutated *Shpingomonas* bacteria of the present invention provides a fermentation broth that includes the exopolysaccharide in a slime form. The viscosity of the fermentation broth is dependent on the amount of sphingan exopolysaccharide that is produced, which is in turn dependent on the amount of sugar converted during the fermentation into exopolysaccharide. If either the sugar concentration at the beginning of the fermentation or the efficiency of conversion of sugar into exopolysaccharide is increased, then the viscosity of the broth will increase correspondingly. For example, a fermentation with *Shpingomonas* strain X287 of about 48 to about 96 hours at a temperature of about 25° C. to about 35° C., results in the production of gellan gum in the slime form. The resulting fermentation broth has a viscosity of about 15,000 to about 30,000 cp, preferably about 15,000 to about 20,000 cp, and from about 20 to about 25 g/L as total biomass. Generally, one-half to three-quarters of this biomass represents the exopolysaccharide itself.

In this aspect of the invention, fermentation broths produced through the fermentation of genetically mutated *Shpingomonas* bacteria of the present invention have a viscosity of less than about 20,000 cp, whereas, fermentation broths produced through the fermentation of corresponding parental strains have a viscosity of more than about 40,000 cp. The reduced viscosity provided by the slime form of the exopolysaccharide results in more efficient mixing and aeration, and lower energy consumption.

Mixing, aeration and energy consumption during fermentation are dependent on the size and shape of the fermentation vessel, the type, size and quantity of the fermentation vessel impellers, and the culture viscosity. For example, with identical fermentation equipment and operating conditions, a wild type parental strain can be grown to stationary phase, which for *Shpingomonas* bacteria is an absorbance at 600 nm exceeding about 15. At stationary phase, the fermentation broth will have no detectable oxygen as measured by oxygen sensors inside the vessel. By contrast, the fermentation broth for a genetically mutated bacteria of the present invention grown to stationary phase will have a dissolved oxygen level of at least about 5 percent saturation of water. In addition, maintenance of a positive oxygen level during the entire duration of a fermentation with a genetically mutated bacteria of the present invention leads to higher rates of production of exopolysaccharides.

Another example of the advantages of producing exopolysaccharide in a less viscous slime form is the possibility of adjusting the pH within the vessel by addition of exogenous acid or base. When the viscosity exceeds about 20,000 cp, as in a fermentation with a parental strain, rapid mixing of acid or base to produce a homogenous solution is not possible. Instead, regions of high concentrations of acid or base are created. Respectively, the concentrated acid or base can hydrolyze the polysaccharide or cleave acyl groups from the polysaccharide. Efficient control of pH during the entire duration of a fermentation can also increase productivity.

In an important aspect, the present invention is effective for providing a fermentation broth that results in improved downstream recovery and processing of sphingan exopolysaccharides as compared to fermentation broths where sphingan exopolysaccharides are produced in a capsule form. In this aspect of the invention, sphingan exopolysaccharides are typically recovered by alcohol precipitation. Volume requirements for alcohol precipitation may be reduced from about 2 volumes to about 1 to about 1.5 volumes per volume of fermentation broth. Further, temperatures for effective precipitation may be reduced from about 90° C. to about 25° C. to about 50° C.

After fermentation, and prior to precipitation with alcohol, the fermentation broth containing exopolysaccharides may be treated by additional processing steps. For example, to kill bacterial cells, the broth temperature may be raised to greater than 80° C. for at least 15 minutes. Acyl groups may be removed from the polysaccharide by adding alkali to the heated broth to achieve a pH of about 9 or higher. In the special case of gellan gum, these two steps cause the fermentation broth viscosity to decrease sufficiently to allow separation of the bacterial cells from the polysaccharide by physical means such as by either filtration or sedimentation by centrifugation, or a combination of the two processes. However, when gellan gum is produced in a capsule form, the separation steps must be accomplished while the fermentation broth temperature is maintained above 80° C. At temperatures below 80° C., gellan gum in the culture broth will solidify into a firm gel with the chains of the gellan crosslinked by divalent cations in the culture medium. If the gellan gum forms a gel, it becomes impossible to recover the gellan by precipitation, and the gelled material must be discarded. By contrast, when the exopolysaccharide is in the slime form, viscosity is reduced and the temperature required to prevent formation of a gel is reduced. In this aspect of the invention, the temperature during the cell-separation step can be reduced to as low as about 60° C.

In accordance with this aspect of the invention, the process yields about 10 to about 20 grams expolysaccharide per liter of broth. The purity typically exceeds at least about 80%.

DETAILED DESCRIPTION

Definitions

Unless defined otherwise, all technical and scientific terms used herein have the same meaning as commonly understood by one of ordinary skill in the art to which this invention belongs. Singleton et al. (1994) Dictionary of Microbiology and Molecular Biology, second edition, John Wiley and Sons (New York) provides one of skill with a general dictionary of many of the terms used in this invention. All patents and publications referred to herein are incorporated by reference herein. For purposes of the present invention, the following terms are defined below.

The terms "sphingan" and "sphingan exopolysaccharide" as used herein refer to a group of related but distinct exopolysaccharides secreted by members of the genus *Shpingomonas* (Pollock, J. Gen. Microbiology 139:1939-1945, 1993). The structures of the sphingans are all somewhat related. The main chain of each sphingan consists of a related sequence of four sugars: D-glucose, D-glucuronic acid, L-mannose and L-rhamnose. Polysaccharide members of the sphingan group are distinguishable from each other by virtue of the carbohydrates which comprise the polymer backbone and the sidechains. The sphingan polysaccharides may contain carbohydrate side chains and acetyl or pyruvyl groups attached to carbohydrates on the polymer backbone. See Mikolajczak, et al., Appl. and Env. Microbiol., 60:402, (1994). Gellan, welan, rhamsan, S-88, S-7, NW-11, S-198 and S-657 are examples of exopolysaccharides in the sphingan group.

Typically, members of the sphingan exopolysaccharide family may be represented by the following general repeating chemical structure:

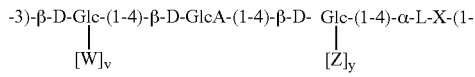

wherein Glc is glucose; GlcA is glucuronic acid or 2-deoxyglucuronic acid; Rha is rhamnose; Man is mannose; X may be Rha or Man; Z is attached to Glc residue 2 and may be α-L-Rha-(1-4)-α-L-Rha, α-L-Man or α-L-Rha; W is attached to Glc residue number 1 and may be β-D-Glc-(1-6)-α-D-Glc, β-D-Glc-(1-6)-β-D-Glc or α-L-Rha, subscripts v and y may be 0, 0.33, 0.5, 0.67 or 1, and wherein the "reducing end" of the polymer is toward the X residue of the backbone. As used herein, the term "backbone" or "main chain" refers to that portion of the structure which excludes chains W and Z, i.e., when v and y are equal to 0.

Some members of the sphingan polysaccharide family are acetylated at various positions. However, the polysaccharides may be subjected to chemical deacylation in a conventional manner to remove the acyl groups. For example, gellan has the same carbohydrate backbone as welan (i.e., X=Rha), but lacks the side chain sugar (i.e., v=0 and y=0) and the glucose residue 1 is fully substituted with glycerate. The gellan subunit structure is also partially acetylated at glucose residue 1. "Deacylated" as used herein means lacking glyceryl and acetyl groups.

As indicated above, one example of a sphingan exopolysaccharide is gellan gum. "Gellan gum" means a polysaccharide having the carbohydrate repeat structure —[(L)rhamnose-(D)glucose-(D)glucuronic acid-(D)glucose]—with glyceryl and acetyl groups attached to the glucose residue immediately to the reducing side of rhamnose. In standard practice the reducing end of an oligosaccharide is placed at the right. Gellan gum has, on average, about one glyceryl group per repeat unit and about one acetyl group per two repeat units.

As further described herein, parental strains of *Shpingomonas* produce sphingan exopolysaccharide in the form of a capsule. As used herein "capsule" means a polysaccharide attached to the surface of the producing bacterial cell, and which remains attached even after aqueous dilution, and which cannot be separated from the attached cells by sedimentation or centrifugation.

The term "*Shpingomonas*" as used herein refers to strains of gram-negative bacteria from the genus *Shpingomonas* which produce exopolysaccharides or sphingans, as described above. The sphingan-producing family of gram-negative bacteria was first identified as belonging to the genus *Shpingomonas* in 1993 (See Pollock, J. Gen. Microb., 139, 1939 (1993)).

*Shpingomonas* bacteria useful in the present invention include *Shpingomonas* bacteria derived from parental strains that are genetically mutated or which have undergone induced mutagenesis.

As used herein "parental strain" means the bacterial strain or an individual bacteria before any treatment such as induced mutagenesis, which is intended to modify the genetic content or phenotype of a parental strain. This is meant to clearly distinguish a parental strain from a mutated or genetically-modified derivative strain that may be obtained from a parental strain or bacteria.

"Genetically mutated" as used herein means the quality of having been subjected to either spontaneous or induced mutagenesis, and exhibiting properties that distinguish the mutated bacteria or strain of bacteria from the parental strain.

"Induced mutagenesis" as used herein means the treatment of bacterial cells with agents commonly known to induce the formation of genetic mutations in DNA, including, but not limited to chemicals, electromagnetic radiation, biological agents such as viruses, plasmids, insertion elements or transposons.

The *Shpingomonas* bacteria of the present invention produce exopolysaccharides in the form of a slime. As used herein "slime" means a polysaccharide which is not attached to the producing bacterial cell and which can be substantially separated from cells by sedimentation or centrifugation of the fermentation broth or after aqueous dilution of the broth, and in the absence of heat treatment, or other physical or chemical treatments of the broth. Bacteria which produce an exopolysaccharide in the form of a slime can be distinguished from those that produce a capsular polysaccharide by observation with a light microscope. The encapsulated *Shpingomonas* bacteria form multicellular aggregates held together by the polysaccharide chains attached to the surfaces of the cells, in contrast to the evenly dispersed slime-forming bacterial cells which have no capsule holding them together in aggregates.

The term "biosynthesis" as used herein describes the biological production or synthesis of sphingan by *Shpingomonas* bacteria. Sphingan exopolysaccharides are synthesized from individual carbohydrate units in a series of steps controlled by a number of enzymes of the bacteria.

The term "biomass" refers to the exopolysaccharide plus bacterial cells in a bacterial culture.

Strain Development

The present invention utilized strains of *Shpingomonas* bacteria which have been genetically mutated to synthesize and secrete sphingan exopolysaccharides in a slime form. In this aspect of the invention, parental *Shpingomonas* strains which produce sphingan exopolysaccharide in a capsule form were subjected to procedures to provide genetically mutated *Shpingomonas* bacteria. Examples of parental strains utilized included S60 (ATCC 31461), S130 (ATCC 31555), S88 (ATCC 31554) and S7 (ATCC 53159). Examples of genetically mutated *Shpingomonas* bacteria useful in the present invention include ATCC PTA-3487 (strain X287) which produces gellan gum in a slime form, ATCC PTA-3486 (strain X530) which produces welan gum in a slime form, ATCC PTA-3485 (strain Z473) which produces exopolysaccharide S-88 in a slime form, and ATCC PTA-3488 (strain X031) which produces exopolysaccharide S-7 in a slime form.

Fermentation

Another aspect of the present invention relates to the enhanced production of sphingan exopolysaccharide. To produce sphingan exopolysaccharide, genetically mutated *Shpingomonas* bacteria are cultured under suitable fermentation conditions, which are well known in the art and which are generally described in U.S. Pat. No. 5,854,034 which is hereby incorporated by reference. To summarize, a suitable medium for culturing the genetically mutated *Shpingomonas* bacteria is an aqueous medium which generally contains a source of carbon such as, for example, carbohydrates including glucose, lactose, sucrose, maltose or maltodextrins, a nitrogen source such as, for example, inorganic ammonium, inorganic nitrate, organic amino acids or proteinaceous materials such as hydrolyzed yeast, soy flour or casein, distiller's solubles or corn steep liquor, inorganic salts and vitamins. A wide variety of fermentation media will support the production of sphingans according to the present invention.

The carbohydrates are included in the fermentation broth in varying amounts but usually between about 1% and 5% by weight of the fermentation medium. The carbohydrates may be added all at once prior to fermentation or alternatively, during fermentation. The amount of nitrogen may range from about 0.01% to about 0.2% by weight of the aqueous medium. A single carbon source or nitrogen source may be used, as well as mixtures of these sources.

Among the inorganic salts which find use in fermenting Shpingomonas bacteria are salts which contain sodium, potassium, ammonium, nitrate, calcium, phosphate, sulfate, chloride, carbonate and similar ions. Trace metals such as magnesium, manganese, cobalt, iron, zinc, copper, molybdenum, iodide and borate may also be advantageously included. Vitamins such as biotin, folate, lipoate, niacinamide, pantothenate, pyridoxine, riboflavin, thiamin and vitamin $B_{12}$ and mixtures thereof may also be advantageously employed.

The fermentation is carried out at temperatures between about 25° and 35° C., with optimum productivity obtained within a temperature range of about 28° C. and 32° C. The inoculum is prepared by standard methods of volume scale-up, including shake flask cultures and small-scale submerged stirred fermentation. The medium for preparing the inoculum can be the same as the production medium or can be any one of several standard media well-known in the art, such as Luria broth or YM medium. The concentration of carbohydrate can be reduced in the seed cultures to less than about 1% by weight. More than one seed stage may be used to obtain the desired volume for inoculation. Typical inoculation volumes range from about 0.5% to about 10% of the total final fermentation volume.

The fermentation vessel typically contains an agitator to stir the contents. The vessel also may have automatic pH and foaming controls. The production medium is added to the vessel and sterilized in place by heating. Alternatively, the carbohydrate or carbon source may be sterilized separately before addition. A previously grown seed culture is added to the cooled medium (generally, at the fermentation temperature of about 28° to about 32° C.) and the stirred culture is fermented for about 48 to about 96 hours, producing a broth having a viscosity of from about 15,000 to about 20,000 cp and from about 10 to about 15 g/L sphingan exopolysaccharide in the slime form. The fermentation of a corresponding parental Shpingomonas bacteria will typically provide a broth having a viscosity of from about 25,000 to about 50,000 cp.

In this aspect, the invention provides an exopolysaccharide in slime form obtained from Shpingomonas bacteria grown in submerged, stirred and aerated liquid culture. The concentration of dissolved oxygen in the liquid culture exceeds about 5% of saturation of water after 24 hours of culturing. Similar fermentations with parental strains resulted in 0% dissolved oxygen after 24 hours. The lower viscosity provided by the exopolysaccharide in slime form results in improved aeration which allows the Shpingomonas bacteria to be productive in culture for a longer period of time.

In another aspect of the present invention, fermentation may be carried out in a semi-batch process where bacteria from one fermentation are used as an inoculum for a subsequent fermentation. In this aspect, Shpingomonas bacteria which have been separated from the exopolysaccharides which they produced may be added to a fresh fermentation broth, or a fresh fermentation broth may be added to the remaining Shpingomonas bacteria. Hence, this aspect of the invention precludes the need to provide a separate seed culture.

Processing of Fermentation Broth

Several approaches may be utilized to further process the fermenation broth for recovery of exopolysaccharides. For example, exopolysaccharides may be directly precipitated from the fermentation broth, the fermentation broth may be first clarified and then precipitated, the fermentation broth may be deacylated followed by precipitation, or the fermentation broth may be deacylated followed by clarification and precipitation.

In one aspect of the invention, a fermentation broth having at least about 1% w/v amount of exopolysaccharides and a viscosity of not more than about 25,000 cp is further processed for recovery of exopolysaccharides. In this aspect of the invention, from about 1 to about 1.5 volumes of alcohol is added directed to the fermentation broth at a temperature of about 25° C. to about 50° C. Alternatively, a fermentation broth may be first deacylated and then clarified prior to addition of alcohol as described in U.S. Pat. No. 4,326,052, which is hereby incorporated by reference. Alcohol effective for the precipitation of exopolysaccharides include ethanol, isopropylalcohol, propanol, butanol, and mixtures thereof. Precipitation may be in batch mode or semi-continuous or continuous mode depending on the type of mixing device used. If mixing is impeded by high viscosity then a dilution with water is used before adding alcohol.

After fermentation, exopolysaccharides are then separated from cellular debris with sedimentation or filtration. Sedimentation may be accomplished by centrifugation. In this aspect of the invention, after precipitation, any of several methods known in the art for recovering, pressing, drying and milling to give a homogenous exopolysaccharide powder can be used.

In accordance with this aspect of the invention, the process yields about 1 to about 2% (w/v, based on the original broth volume) exopolysaccharide. The purity typically exceeds at least about 80%.

The following examples illustrate methods for carrying out the invention and should be understood to be illustrative of, but not limiting upon, the scope of the invention which is defined in the appended claims.

EXAMPLES

Example I

Gellan gum was produced from the Shpingomonas mutant strain X287, which is derived from the wild type strain ATCC31461, and from the ATCC31461 parent strain by aerated, stirred, submerged fermentation. Strain X287 was obtained by a reproducible multi-step regimen of induced mutagenesis and selection of preferred properties.

The growth medium contained (per liter of deionized water): 1 g ammonium nitrate, 0.5 g soluble hydrolyzed soy protein (Soy Peptone from Marcor), 3.2 g dibasic potassium phosphate, 1.6 g monobasic potassium phosphate, 0.1 g magnesium sulfate (heptahydrate), trace minerals, and glucose. The trace minerals contained (per liter of final medium): 2.7 mg $FeCl_3$-$6H_2O$, 1.36 mg $ZnCl_2$, 1.98 mg $MnCl_2$-$4H_2O$, 240 µg $CoCl_2$-$6H_2O$, 240 µg $Na_2MoO_4$-$2H_2O$, and 250 µg $CuSO_4$-$5H_2O$. The final fermentation medium contained 25 g glucose per liter, and the preculture medium contained 10 g glucose per liter.

A vial of frozen cells was thawed and added to a preculture of 500 ml in a baffled flask and incubated at 30° C. on a rotary shaker for about 16-20 hours or until the cell density measured by the absorbance at 600 nm was about 3-5. The frozen cells were samples taken from a previous preculture flask which had been inoculated with a single colony of the bacterial strain grown on an agar plate containing the same medium.

An amount of a preculture was added to the fermentor to give an inoculation of about 5-10% by volume. The fermentor was either a New Brunswick model III or model 3000 and contained 4 liter of medium. The fermentor was aerated with 1 volume of air per volume of fermentation medium, and was maintained at 30° C. The agitation speed was controlled by the amount of dissolved oxygen which was set to a minimum of 30% of saturation. During the fermentations the agitation speed reached the maximum of 1000 rpm and this was followed by a decrease in the level of dissolved oxygen to between 0-30%.

The following table shows the results of submerged fermentations with the parent strain ATCC31461 and the slime-forming mutant strain X287. For the X287 mutant culture where the polysaccharide is not attached to the cells, the reduced viscosity results in more efficient mixing and aeration, and lower energy consumption.

| Strain | Duration (hr) | A600 | IPA precipitate (g/l) | Glucose consumed (g/l) | Viscosity (cp at 12 rpm) |
|---|---|---|---|---|---|
| ATCC31461 | 27 | 16.7 | 12.8 | 22.7 | 21700 |
| X287 | 32 | 15.7 | 15.1 | 24.4 | 12900 |

During product recovery by alcohol precipitation two volumes of isopropylalcohol are required to precipitate gellan gum made by the wild type strain ATCC31461. In contrast the gellan gum made in the form of a slime by strain X287 is precipitated from the broth with only one volume of isopropylalcohol. In addition, the gellan gum made in the form of a slime can be precipitated with isopropylalcohol at 25-30° C. while the wild type gellan requires a heating step before adding the alcohol.

Example II

Welan gum was produced in slime form from any of several mutant strains, of which strains X530 and X319 are representative, which were obtained by multi-step regimen applied to the wild type parent strain ATCC31555, consisting of induced or spontaneous mutagenesis and selection of preferred properties.

Bacterial strain X530 was grown in liquid medium (described in Example I) in shaking flasks. Strain X530 synthesized welan gum which was unattached to the cells, in the form of a slime. The appearance of the culture was observed with a light microscope. Whereas the parental wild type strain formed multicellular aggregates held together by the capsular polysaccharides attached to each cell, the cells of strain X530 did not form aggregates and were free to distribute evenly throughout the culture medium as single cells. The following measurements were made and are tabulated below: culture viscosity (centipoise at 12 rpm with spindle #4 for a Brookfield LVTDV-II viscometer), cell density (absorbance at 600 nm), and weight of the biomass (polysaccharide plus cells) precipitated directly from the culture broth at 25° C. with 2 volumes of isopropylalcohol (g/l).

| Strain | Cell Density A600 | Culture Viscosity cp | Precipitated Biomass g/l |
|---|---|---|---|
| ATCC 31555 | 14.7 | 6610 | 7.8 |
| ATCC 31555 | 14.8 | 8300 | 8.3 |
| X530 slime | 14.7 | 5910 | 9.8 |
| X319 slime | 17.7 | 4960 | 8.7 |

In addition, the precipitations were performed at 90° C. and the appearance of the precipitated polysaccharides in the alcohol-broth mixtures was recorded. Addition of 2 volumes of isopropylalcohol to the culture of strain X530 caused the formation of cohesive clots at either 25° C. or 90° C., while in contrast the precipitated polysaccharides for the wild type parent strain formed dispersed fragmented clots at 25° C. and cohesive clots at 90° C.

Example III

Polysaccharide S-88 was produced in slime form from any of several mutant strains, of which strains X099 and Z473 are representative, which were obtained by a multi-step regimen applied to the wild type parent strain ATCC31554, consisting of induced or spontaneous mutagenesis and selection of preferred properties.

The growth medium contained (per liter of water): 1 g ammonium nitrate, 0.5 g soluble hydrolyzed soy protein (Soy Peptone from Marcor), 3.2 g dibasic potassium phosphate, 1.6 g monobasic potassium phosphate, 0.2 g magnesium sulfate (heptahydrate), trace minerals, and glucose. The trace minerals contained (per liter of final medium): 2.7 mg $FeCl_3$-$6H_2O$, 1.36 mg $ZnCl_2$, 1.98 mg $MnCl_2$-$4H_2O$, 240 µg $CoCl_2$-$6H_2O$, 240 µg $Na_2MoO_4$-$2H_2O$, and 250 µg $CuSO_4$-$5H_2O$. The final fermentation medium contained 30 g glucose per liter, and the preculture medium contained 20 g glucose per liter.

A vial of frozen cells was thawed and added to a preculture of 500 ml in a baffled flask and incubated at 30° C. on a rotary shaker for about 16-20 hours or until the cell density measured by the absorbance at 600 nm was about 3-5. The frozen cells were samples taken from a previous preculture flask which had been inoculated with a single colony of the bacterial strain grown on an agar plate containing the same medium.

An amount of a preculture was added to the fermentor to give an inoculation of about 5-10% by volume. The fermentor was a New Brunswick model III and contained 4 liter of medium. The fermentor was aerated with 1 volume of air per volume of fermentation medium, and was maintained at 30° C. The agitation speed was controlled by the amount of dissolved oxygen which was set to a minimum of 30% of saturation. During the fermentations the agitation speed reached the maximum of 1000 rpm and this was followed by a decrease in the level of dissolved oxygen to between 0-30%.

The following table shows the results of submerged fermentations with the parent strain ATCC31554 and the slime-forming mutant strains X099 and Z473. For the X099 and Z473 mutant cultures where the polysaccharide is not attached to the cells, the productivity is increased, as indicated by the increased viscosity of the broth and the increased weight of the IPA precipitate. The polysaccharide precipitated with only one volume of isopropylalcohol per volume of culture broth, in contrast to two volumes for the wild type parent ATCC31554. The cells of strains X099 and Z473 can be removed from the polysaccharide by slow speed centrifugation (about 5000×G), which was not possible with the ATCC31554 wild type parent strain.

| Strain | Duration (hr) | A600 | IPA precipitate (g/l) | Glucose consumed (g/l) | Viscosity (cp at 12 rpm) |
|---|---|---|---|---|---|
| ATCC31554 | 36 | 14.0 | 11.6 | 21.9 | 8600 |
| X099 | 36 | 15.8 | 15.0 | 23.1 | 14300 |
| Z473 | 36 | 15.7 | 12.0 | 20.8 | 13100 |

Example IV

Polysaccharide S-7 was produced in slime form from a mutant strain X031 and in capsule form by ATCC21423 when cultured by fermentation. Strain X031 is a spontaneous mutant derived from the ATCC 21423 strain. The growth medium contained (per liter of water) 1 g ammonium nitrate, 0.5 g soluble hydrolyzed soy protein (Soy Peptone from Marcor), 3.2 g dibasic potassium phosphate, 1.6 g monobasic potassium phosphate, 0.2 g magnesium sulfate (heptahydrate), trace minerals, and glucose. The trace minerals contained (per liter of final medium): 2.7 mg $FeCl_3\text{-}6H_2O$, 1.36 mg $ZnCl_2$, 1.98 mg $MnCl_2\text{-}4H_2O$, 240 µg $CoCl_2\text{-}6H_2O$, 240 µg $Na_2MoO_4\text{-}2H_2O$, and 250 µg $CuSO_4\text{-}5H_2O$. The final fermentation medium contained 30 g glucose per liter, and the preculture medium contained 20 g glucose per liter.

A vial of frozen cells was thawed and added to a preculture of 500 ml in a baffled flask and incubated at 30° C. on a rotary shaker for about 16-20 hours or until the cell density measured by the absorbance at 600 nm was about 3-5. The frozen cells were samples taken from a previous preculture flask which had been inoculated with a single colony of the bacterial strain grown on an agar plate containing the same medium.

An amount of a preculture was added to the fermentor to give an inoculation of about 5-10% by volume. The fermentor was a New Brunswick model III and contained 4 liter of medium. The fermentor was aerated with 1 volume of air per volume of fermentation medium, and was maintained at 30° C. The agitation speed was controlled by the amount of dissolved oxygen which was set to a minimum of 30% of saturation. During the fermentations the agitation speed reached the maximum of 1000 rpm and this was followed by a decrease in the level of dissolved oxygen to between 0-30%.

The following table shows the results of submerged fermentations with the parent strain ATCC21423 and the slime-forming mutant strain X031. For the X031 mutant culture where the polysaccharide is not attached to the cells, the reduced viscosity results in more efficient mixing and aeration, and lower energy consumption. The cells of strain X031 could be removed from the polysaccharide by slow speed centrifugation (about 5000×G), which was not possible with the ATCC21423 wild type parent strain. The cells of the wild type strain ATCC21423 were only removed by slow speed centrifugation after partial hydrolysis of the polysaccharide with elevated temperature (about 90-121° C.) with the pH in the acidic range of 5-7. By breaking the polysaccharide chains at internal positions in the polymers the cells and a fraction of the polysaccharide became disconnected.

| Strain | Duration (hr) | A600 | IPA precipitate (g/l) | Glucose consumed (g/l) | Viscosity (cp at 12 rpm) |
|---|---|---|---|---|---|
| ATCC21423 | 48 | 8.5 | 17.0 | 26.0 | 31100 |
| X031 | 48 | 9.6 | 17.7 | 30.5 | 20400 |

Example V

*Shpingomonas* mutant strain X287 and its parental strain ATCC31461 were cultured by submerged aerated liquid fermentation as in Example I. The following table shows the time course of changes in viscosity and dissolved oxygen during the duration of the fermentation.

| Strain | Duration (Hrs) | Dissolved Oxygen (%) | Viscosity (cp) |
|---|---|---|---|
| ATCC31461 | 12 | 29 | 250 |
|  | 24 | 0 | 18,000 |
|  | 48 | 0 | 26,400 |
|  | 72 | 0 | 29,700 |
| X287 | 12 | 36 | 725 |
|  | 24 | 28 | 6,460 |
|  | 48 | 10 | 11,000 |
|  | 72 | 0 | 14,200 |

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A fermentation broth comprising slime-forming Sphingomonas bacterial cells selected from the group consisting of ATCC PTA-3487, ATCC PTA-3486, ATCC PTA-3485, ATCC PTA-3488, and mixtures thereof and an exopolysaccharide in slime form that is obtained by a process comprising:
    culturing a *Sphingomonas* bacteria selected from the group consisting of ATCC PTA-3487, ATCC PTA-3486, ATCC PTA-3485, ATCC PTA-3488, and mixtures thereof for a time and temperature effective for providing a broth from which a sphingan exopolysaccharide can be recovered with an alcohol precipitation method at a temperature of about 25° C. to about 50° C.
    wherein the method yields at least about 10 grams of sphingan exopolysaccharide per liter of broth.

2. A fermentation broth according to claim 1 wherein fermentation is conducted from about 48 to about 96 hours at a temperature of about 25° C. to about 35° C.

3. A fermentation broth according to claim 1 wherein in the alcohol precipitation method from about 1 to about 1.5 volumes of alcohol are added to the fermentation broth.

4. A fermentation broth comprising slime-forming *Sphingomonas* bacterial cells and an exopolysaccharide in a slime form, wherein the exopolysaccharide can be recovered from said fermentation broth by alcohol precipitation at a temperature of about 25° C. to about 50° C. to yield at least about 10 grams of exopolysaccharide per liter of broth, and wherein the *Sphingomonas* is selected from the group consisting of ATCC PTA3487, ATCC PTA-3486, ATTC PTA-3485, ATCC PPA-3488, and mixtures thereof.

5. A fermentation broth according to claim 4 wherein the exopolysaccharide in slime form is a sphingan exopolysaccharide having the general formula

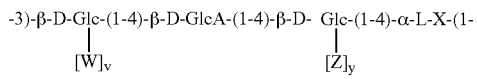

wherein Glc is glucose, GlcA is glucuronic acid or 2-deoxy-glucuronic acid, Rha is rhamnose, Man is mannose, X is Rha or Man, Z is attached to Glc residue 2 and is α-L-Rha-(1-4)-α-L-Rha, α-L-Man or α-L-Rha, W is attached to Glc residue number 1 and is β-D-Glc-(1-6)-α-D-Glc, β-D-Glc-(1-6)-β-D-Glc or α-L-Rha, subscripts v and y are 0, 0.33, 0.5, 0.67 or 1.

6. A fermentation broth comprising slime-forming *Sphingomonas* bacterial cells and an exopolysaccharide in a slime form having the general formula

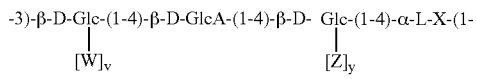

wherein Glc is glucose, GlcA is glucuronic acid or 2-deoxy-glucuronic acid, Rha is rhamnose, Man is mannose, X is Rha or Man, Z is attached to Glc residue 2 and is α-L-Rha-(1-4)-α-L-Rha, α-L-Man or α-L-Rha, W is attached to Glc residue number 1 and is β-D-Glc-(1-6)-α-D-Glc, β-D-Glc-(1-6)-β-D-Glc or α-L-Rha, subscripts v and y are 0, 0.33, 0.5, 0.67 or 1, wherein the fermentation broth has at least about 1% w/v exopolysaccharide and a viscosity of not more than about 25,000 cp, and wherein the *Sphingomonas* is selected from the group consisting of ATCC PTA-3487, ATCC PTA3486, ATCC PTA-3485, ATCC PTA-3488, and mixtures thereof.

7. A fermentation broth comprising slime-forming *Shpingomonas* bacteria selected from the group consisting of ATCC PTA-3487, ATCC PTA-3486, ATCC PTA-3485, ATCC PTA-3488, and mixtures thereof and an exopolysaccharide in a slime form produced by the *Shpingomonas* bacteria, wherein the *Shpingomonas* bacteria are grown in a submerged, aerated liquid culture, wherein a concentration of dissolved oxygen exceeds about 5% of saturation of water after 24 hours of culturing, and wherein the exopolysaccharide in slime form is produced by *Shpingomonas* selected from the group consisting of ATCC PTA-3487, ATCC PTA-3486, ATCC PTA-3485, ATCC PTA-3488, and mixtures thereof.

8. A fermentation broth according to claim 7 wherein the exopolysaccharide in slime form is a *Sphingomonas* exopolysaccharide having the general formula

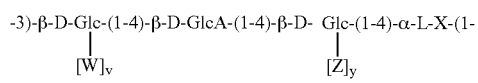

wherein Glc is glucose, GlcA is glucuronic acid or 2-deoxy-glucuronic acid, Rha is Rhamnose, Man is mannose, X is Rha or Man, Z is attached to Glc residue 2 and is α-L-Rha-(1-4)-α-L-Rha, α-L-Man or α-L-Rha, W is attached to Glc residue number 1 and is β-D-Glc-(1-6)-α-D-Glc, βD-Glc-(1-6)-β-D-Glc or α-L-Rha, subscripts v and y are 0, 0.33, 0.5, 0.67 or 1.

9. The fermentation broth of claim 4 wherein the exopolysaccharide is selected from the group consisting of gellan, welan, rhamsan, S-88, S-7, S-198, NW-11 and S-657.

10. The fermentation broth of claim 9 wherein the exopolysaccharide is selected from the group consisting of gellan, welan, S-7 and S-88.

* * * * *

UNITED STATES PATENT AND TRADEMARK OFFICE
CERTIFICATE OF CORRECTION

PATENT NO. : 7,390,644 B2  Page 1 of 1
APPLICATION NO. : 10/617371
DATED : June 24, 2008
INVENTOR(S) : Motohide Yamazaki et al.

It is certified that error appears in the above-identified patent and that said Letters Patent is hereby corrected as shown below:

<u>Title Page, Item 75</u>
Inventor Marcia Mikolajczak's residence, "Encinatas" should read as --Encinitas--.

<u>Column 12</u>
Claim 4, line 66, "ATCC PTA3487" should read --ATCC PTA-3487--.

Claim 4, lines 66-67, "ATCC PPA3488" should read --ATCC PTA-3488--.

<u>Column 13</u>
Claim 6, line 37, "ATCC PTA3486" should read --ATCC PTA-3486--.

<u>Column 14</u>
Claim 8, line 15, "Sphingomonas" should read --sphingan--.

Claim 8, line 29, "βD" should read --β-D--.

Signed and Sealed this

Twenty-first Day of April, 2009

JOHN DOLL
*Acting Director of the United States Patent and Trademark Office*